United States Patent
Chisena

(10) Patent No.: US 11,104,011 B2
(45) Date of Patent: Aug. 31, 2021

(54) MECHANICAL ROBOT ARM ASSEMBLY

(71) Applicant: Robert Chisena, Ann Arbor, MI (US)

(72) Inventor: Robert Chisena, Ann Arbor, MI (US)

( * ) Notice: Subject to any disclaimer, the term of this patent is extended or adjusted under 35 U.S.C. 154(b) by 0 days.

(21) Appl. No.: 15/811,008

(22) Filed: Nov. 13, 2017

(65) Prior Publication Data
US 2018/0126564 A1 May 10, 2018

Related U.S. Application Data

(60) Provisional application No. 62/420,212, filed on Nov. 10, 2016.

(51) Int. Cl.
*B25J 18/00* (2006.01)
*B25J 17/02* (2006.01)
*A61B 1/00* (2006.01)

(52) U.S. Cl.
CPC ......... *B25J 18/007* (2013.01); *A61B 1/00149* (2013.01); *B25J 17/0258* (2013.01); *B25J 17/0291* (2013.01); *A61B 1/0016* (2013.01)

(58) Field of Classification Search
CPC .. B25J 18/007; B25J 17/0258; B25J 17/0291; B25J 17/025; B25J 9/1045; B25J 9/104; A61B 1/00149; A61B 1/0016
USPC .............. 74/490.01, 490.05, 490.06; 901/15
See application file for complete search history.

(56) References Cited

U.S. PATENT DOCUMENTS

| | | | | |
|---|---|---|---|---|
| 3,631,737 A | * | 1/1972 | Wells | B25J 9/06 74/469 |
| 4,283,165 A | * | 8/1981 | Vertut | B25J 5/007 280/771 |
| 4,499,784 A | * | 2/1985 | Shum | B25J 17/0291 414/5 |
| 4,657,472 A | * | 4/1987 | Zimmer | B25J 17/0291 414/735 |
| 4,685,349 A | * | 8/1987 | Wada | B25J 9/06 414/680 |
| 4,690,012 A | * | 9/1987 | Dahlquist | B25J 17/0291 74/417 |
| 4,751,821 A | * | 6/1988 | Birchard | A61F 2/58 60/527 |
| 4,771,652 A | * | 9/1988 | Zimmer | B25J 17/0291 74/640 |
| 4,904,148 A | * | 2/1990 | Larsson | B25J 9/04 414/680 |
| 4,990,050 A | * | 2/1991 | Tsuge | B23Q 1/54 414/735 |

(Continued)

*Primary Examiner* — Jake Cook
*Assistant Examiner* — T. Scott Fix
(74) *Attorney, Agent, or Firm* — The Dobrusin Law Firm, PC

(57) ABSTRACT

A mechanical arm assembly is generally presented. The mechanical arm assembly comprises a plurality of joints including a first joint, one or more intermediate joints, and a terminal joint connected in consecutive series and each configured to rotate with respect to any respective adjacent joints. The first, intermediate, and terminal joints are configured with their base and top arranged at a given angle with respect to the normal plane of the joint, such as parallel to the normal plane or 22.5 degrees with respect to the normal plane. Rotation of the joints is controlled by control wires. The control wires may be routed internally through the joints or externally outside of the joints.

26 Claims, 15 Drawing Sheets

(56) References Cited

U.S. PATENT DOCUMENTS

| | | | | |
|---|---|---|---|---|
| 4,997,413 A * | 3/1991 | Dahlquist | ............. | B25J 17/025 |
| | | | | 475/163 |
| 6,082,290 A * | 7/2000 | Conlin | ................ | B05B 13/0431 |
| | | | | 118/326 |
| 6,796,203 B2 * | 9/2004 | Dubrowskij | ..... | A61B 17/00234 |
| | | | | 74/423 |
| 7,047,835 B2 * | 5/2006 | Yamagishi | ................ | B25J 9/06 |
| | | | | 446/353 |
| 7,597,025 B2 * | 10/2009 | Narita | ....................... | B25J 9/06 |
| | | | | 74/490.02 |
| 7,836,788 B2 * | 11/2010 | Kamon | ..................... | B25J 9/06 |
| | | | | 74/490.01 |
| 8,234,949 B2 * | 8/2012 | Pan | .......................... | B25J 9/104 |
| | | | | 74/490.04 |
| 8,245,594 B2 * | 8/2012 | Rogers | .................. | A61B 17/29 |
| | | | | 294/111 |
| 8,833,197 B2 * | 9/2014 | Zubiate | ..................... | B25J 9/06 |
| | | | | 74/490.04 |
| 9,221,179 B2 * | 12/2015 | Hinman | ................ | A61B 17/29 |
| 9,357,984 B2 * | 6/2016 | Malkowski | ...... | A61B 17/00234 |
| 9,550,299 B2 * | 1/2017 | Wolf | .................... | B25J 17/0275 |
| 2004/0129103 A1 * | 7/2004 | Kamon | ..................... | B25J 9/06 |
| | | | | 74/490.01 |
| 2004/0195988 A1 * | 10/2004 | Buckingham | ............. | B25J 9/06 |
| | | | | 318/560 |
| 2008/0229862 A1 * | 9/2008 | Nakamoto | ............ | B25J 9/1045 |
| | | | | 74/490.04 |
| 2010/0116081 A1 * | 5/2010 | Pistor | .................... | A61B 1/055 |
| | | | | 74/490.05 |
| 2010/0263470 A1 * | 10/2010 | Bannasch | ................ | B25J 9/104 |
| | | | | 74/490.05 |
| 2013/0145891 A1 * | 6/2013 | Long | ....................... | B25J 18/00 |
| | | | | 74/490.02 |
| 2013/0255410 A1 * | 10/2013 | Lee | ........................ | F16H 19/08 |
| | | | | 74/89.22 |
| 2016/0008989 A1 * | 1/2016 | Bakir | ........................ | B25J 9/12 |
| | | | | 74/490.03 |
| 2016/0052130 A1 * | 2/2016 | Ekas | ........................ | B25J 15/0009 |
| | | | | 74/490.04 |
| 2016/0338571 A1 * | 11/2016 | Haraguchi | ........... | A61B 1/0052 |
| 2017/0210015 A1 * | 7/2017 | Jogasaki | ..................... | B25J 9/104 |
| 2018/0200895 A1 * | 7/2018 | Kan | ....................... | A61B 34/30 |

* cited by examiner

MECHANICAL ROBOT ARM ASSEMBLY

CROSS REFERENCE TO RELATED APPLICATION

This application claims priority to U.S. Provisional Patent Application No. 62/420,212 filed on Nov. 10, 2016 and entitled MECHANICAL ROBOT ARM ASSEMBLY, the disclosure of which is hereby incorporated by reference.

FIELD OF INVENTION

The present invention generally relates to the field of mechanically controlled directional devices and more specifically to a unique snake shaped mechanically controlled arm capable of utility across numerous fields of use.

BACKGROUND

Endoscopic surgery or therapeutic endoscopy (as opposed to diagnostic endoscopy) is a quickly growing area of medicine. Patients prefer endoscopic surgeries because of their minimally-invasive nature, clinics and hospitals prefer these surgeries because they increase patient throughput, and healthcare payers prefer these surgeries because they cost less compared to open and laparoscopic surgeries.

The requirements for training physicians to perform procedures using current scope technology, however, limits the penetration of therapeutic endoscopy. For example, endoscopic suturing requires approximately 20 monitored cases and endoscopic removal of gastric carcinoma requires approximately 100 monitored cases before a physician feels comfortable with the procedure.

Current endoscope technology has not changed much since it was first developed in the 1960s. By and large, the scope consists of a narrow, distal insertion section and a proximal hand-control section. The most distal portion of the scope is controlled by guidewires that run the length of the scope and that cause motion in the plane perpendicular to the general axis of the scope. However, this type of design suffers from numerous drawbacks.

One drawback that typical endoscope designs suffer from is lack of full and accurate spatial control. Typical endoscopes utilize a flexible scope that relies on being pushed forward and flexing with the geometry of the tube or cavity in which it is located. However, in a larger cavity it is often difficult to place the tip or tool of the endoscope in a desired location because fine spatial movement of the endoscope tip is difficult to control.

Outside of the medical field, other types of scopes, mechanical snakes, and robotic arms are designed to maneuver in unique and remote spatial areas. For example, industrial applications, such as in manufacturing or three-dimensional printing, robotic arms are commonly used to spatially maneuver to desired coordinates. However, in some applications, environmental conditions, such as heat or moisture, are not conducive to electronics within the robotic arm.

Accordingly, an improved mechanical robotic arm is needed in the industry.

SUMMARY

A mechanical arm assembly is generally presented. The mechanical arm assembly comprises a plurality of joints including a first joint, one or more intermediate joints, and a terminal joint connected in consecutive series and each configured to rotate with respect to any respective adjacent joints. Each joint includes a base, a top, and a sidewall interconnecting the base and the top.

In an embodiment, a normal plane of each joint is defined as generally perpendicular to the sidewall, and the base and top each are arranged at an angle with respect to the normal plane. The first joint is configured with its base generally parallel to its normal plane, and its top at an angle between 10 and 80 degrees with respect to its normal plane. The intermediate joints are configured with their bases at an angle between 10 and 80 degrees in a first direction with respect to their normal plane and their tops at an angle between 10 and 80 degrees in a second direction, opposite the first direction, with respect to its normal plane. The terminal joint is configured with its base at an angle between 10 and 80 degrees with respect to its normal plane and its top generally parallel to its normal plane and its top.

The mechanical arm assembly may include a head protruding from the base of each or some of the joints and an opening in the top of each or some of the joints. The head may be configured to be inserted into the opening in the top of the respective adjacent intermediate or base joint. A bearing may be positioned around the head and configured to insert into the opening in the top of each respective adjacent intermediate and first joint to form a rotational connection between adjacent joints.

The mechanical arm assembly may include one or more control wires connected to the joints and configured to control the rotational movement of the joints to alter the shape and spatial configuration of the mechanical arm assembly.

In an embodiment, an end tool, such as a camera, medical device, or the like, may be connected to the terminal joint.

In an embodiment, the base may include an opening that extends through the inner volume and through the top. The one or more control wires may each extend through the opening of each intermediate joint between the controlled joint and the first joint and through the opening in the first joint.

In an embodiment, one or more control wires includes a knot therein. The head may include a divot and the knot may be positioned in the divot of each corresponding head. Each respective bearing may be positioned around the respective heads to hold the control wires in place.

In an embodiment, the mechanical arm assembly may include a disc having a hole therein and positioned around the head such that the head protrudes through the hole. The disc may be configured to be rotatable with respect to the head. One or more control wires may pass through a disc on a given controlled joint, with each control wire extending toward the first joint and positioned exterior to each joint in the mechanical arm assembly. The disc may include one or more through-holes, and the one or more control wires may be routed through respective through-holes. A channel may be located adjacent to or integral with the through holes and configured to guide the control wires toward the head. The control wires may be wound around the head 1-4 times to facilitate rotation of the joint when tension is applied to the control wires.

BRIEF DESCRIPTION OF THE DRAWINGS

The operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
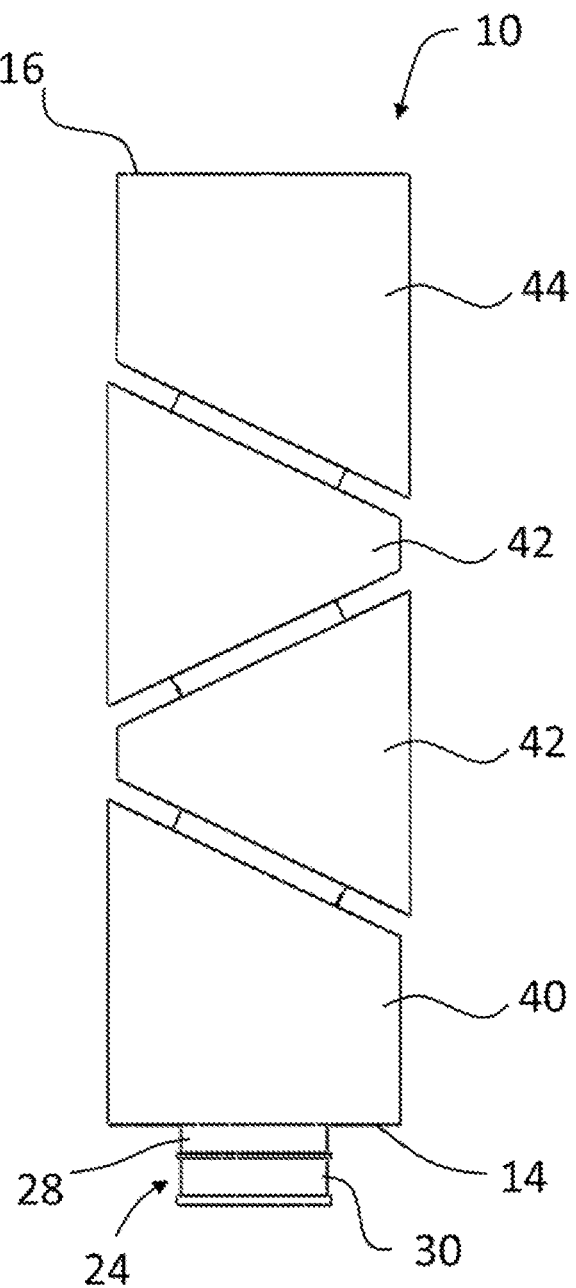
FIG. 1 illustrates a robot arm assembly in a linear formation.

A mechanically controlled arm 10 is generally presented, as shown in FIG. 1. The arm 10 is configured to navigate a spatial opening such as a cavity, tubular space, or the like.

As illustrated in FIGS. 1-11 the arm 10 may comprise a plurality of joints 12. The joints 12 may be formed of any appropriate material, such as plastic, polymer, and the like. The joints 12 may interconnect to form the arm 10 having a length defined between a proximal end 14 and a distal end 16. The joints 12 may rotationally interconnect to one another to allow the arm 10 to navigate a spatial region, as described in further detail below.

Each joint 12 may be generally cylindrically shaped, having a base 18, a top 20, and an outer wall 22. The base 18 may comprise a generally flat, solid surface at the proximal end of the joint 12. A head 24 may protrude from the surface of the base 18 outwardly, away from the joint 12 in a direction perpendicular to the base 18. The head 24 may be generally cylindrically shaped and configured to interconnect with and provide a rotational connection with an adjacent joint 12, as described in further detail below.

Figure 5:
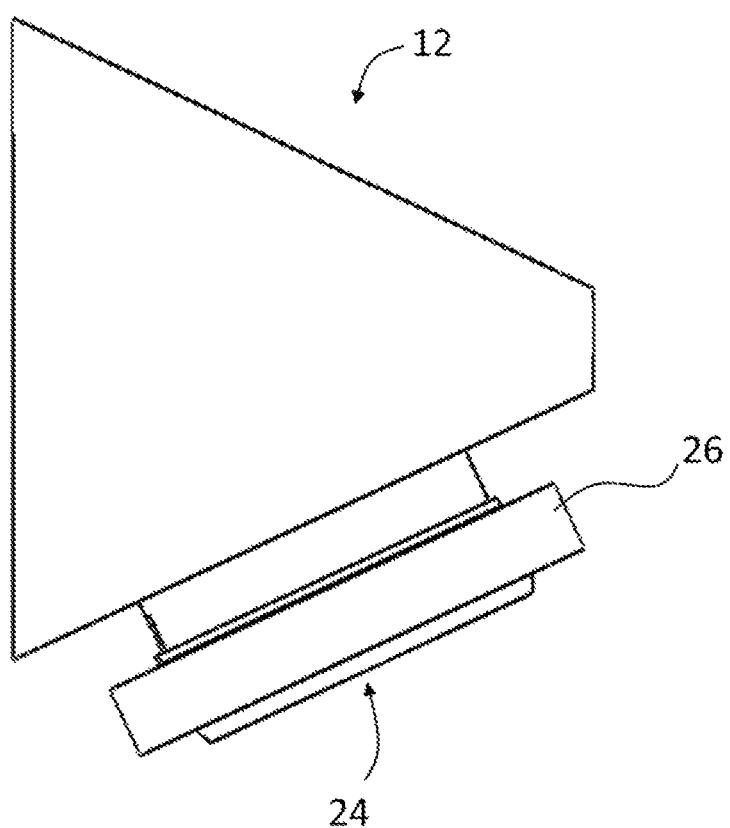
FIG. 5 illustrates a joint having an attached bearing.

The head 24 may be configured to receive a bearing 26 thereon to facilitate the rotational engagement between adjacent joints 12. For example, the head 24 may include or be divided into an upper portion 28 and a lower portion 30. The upper and lower portions 28, 30 of the head may be separated by a ledge, such as that protrudes outward from the head 24 or a ledge formed by the upper portion 28 having a larger diameter than the lower portion 30. The lower portion 30 may be configured to receive a bearing 26 thereon. The bearing 26 may be formed of any appropriate material such as a metal. The bearing 26 may be circular or ring-shaped having an opening sized and shaped to receive the lower portion 30 there-through. When seated on the head 24, the bearing 26 may be positioned near the ledge, leaving the space of the upper portion 28 open between the bearing 26 and the base 18, as shown in FIG. 5. The bearing 26 may include an inner surface configured to connect to the lower portion 30 by a compression fit, snap fit, or the like, and an outer surface configured to rotate with respect to the inner surface.

The top 20 of the joint 12 may be generally open providing access into the inner volume 32 of the cylindrical joint 12. For example, the top surface 20 may comprise a ring, circular, or ovular surface at the distal end of the cylindrical body of the joint 12. In some embodiments, the top surface ring 20 may be angled with respect to the base 18, such as non-parallel to the base 18, as shown in the FIG. 3 and described in further detail below. The top 20 may define an opening to the inner volume 32, which may be sized and shaped to receive the bearing 26 and head 24 of an adjacent joint 12 therein. Specifically, the inner volume 32 may be sized and shaped to receive and retain a bearing 26 in a compression fit to provide a rotational connection between adjacent joints 12. For example, the interior perimeter of the inner volume may include one or more snap posts 39, such as four snap posts 39 equally spaced about the top opening into the interior volume 32. Each snap post 39 may comprise a protrusion configured to hold the bearing 26 in a compression or snap fit within the inner volume 32.

Figure 2A:
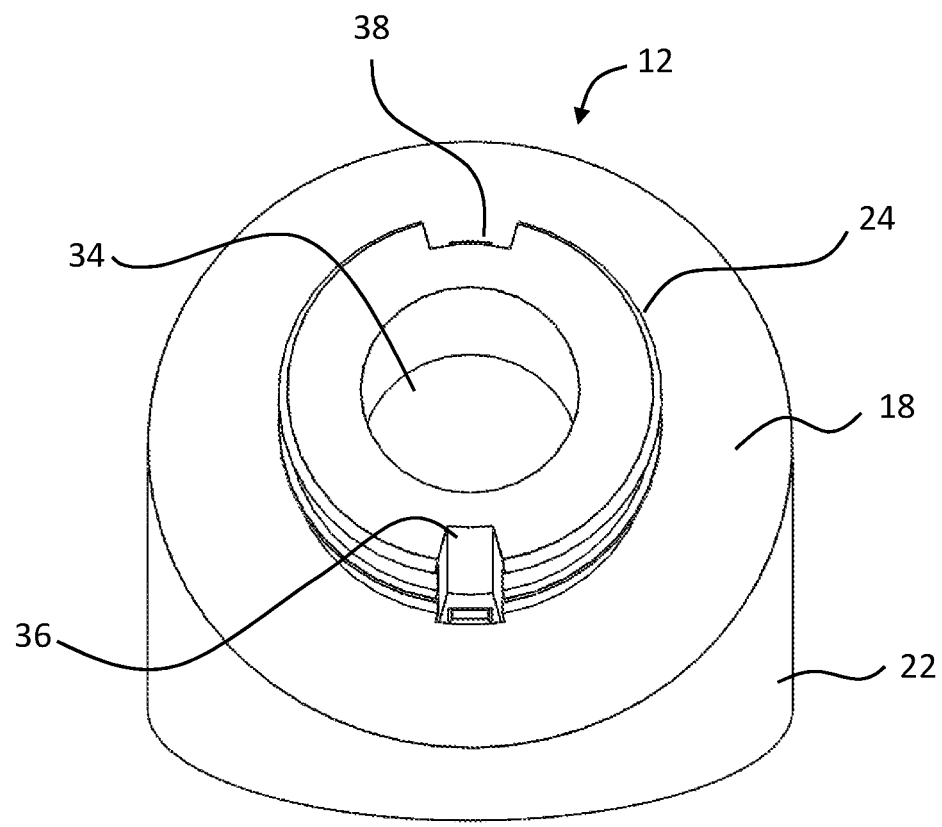
FIG. 2a illustrates a bottom-front perspective view of a joint of the robot arm assembly.
Figure 2B:
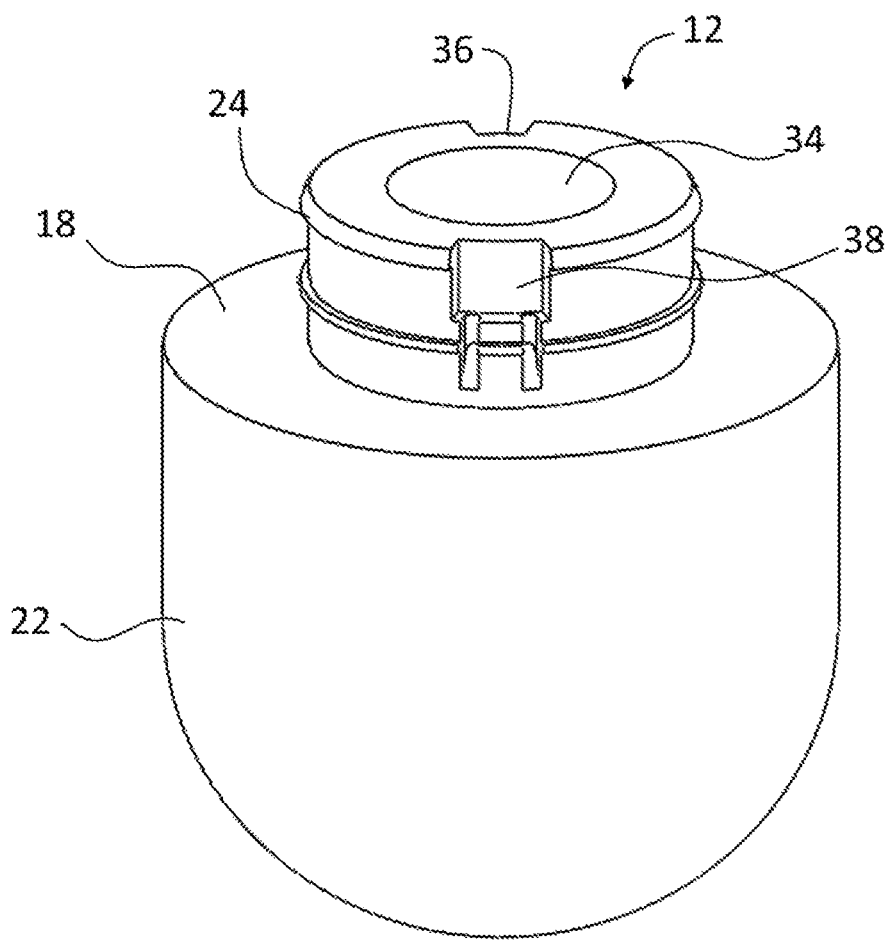
FIG. 2b illustrates a bottom-rear perspective view of a joint of the robot arm assembly.
Figure 3:
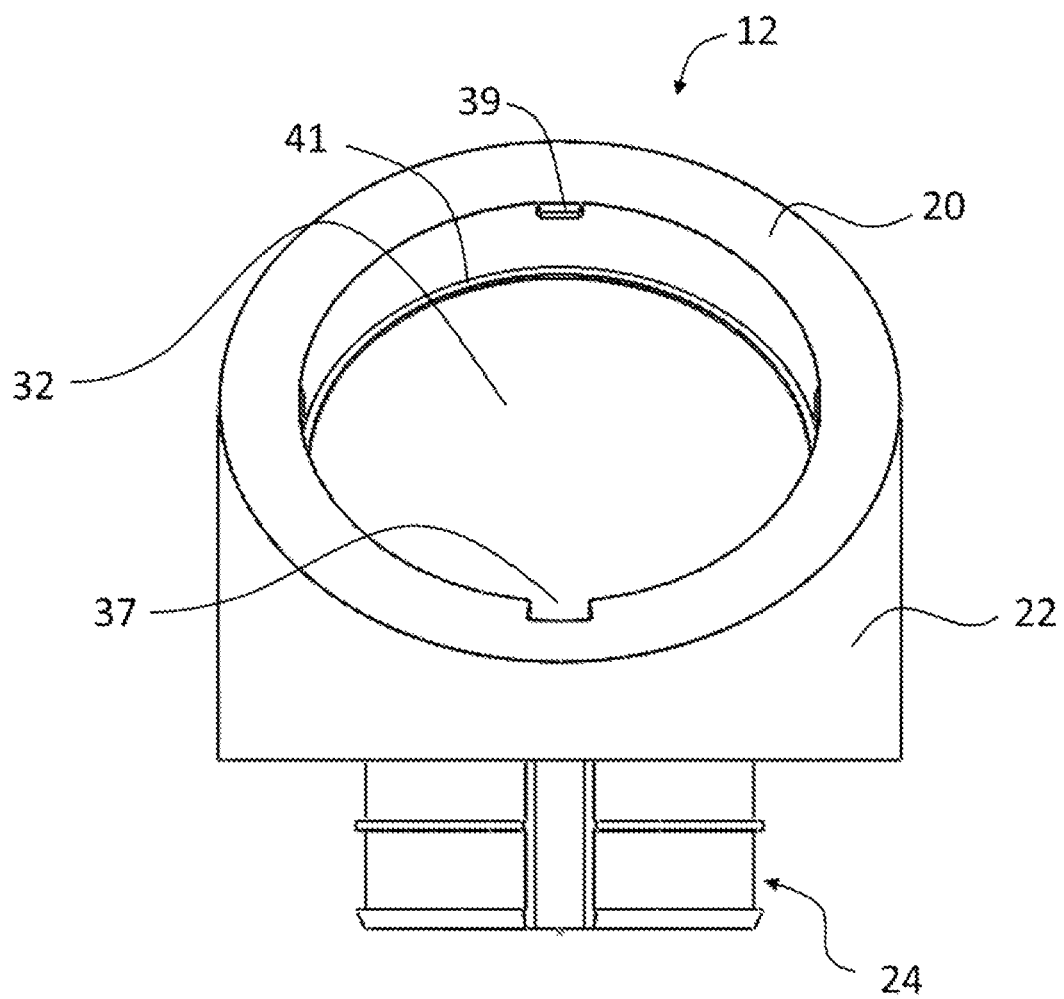
FIG. 3 illustrates a top-front perspective view of a joint of the robot arm assembly.
Figure 4:
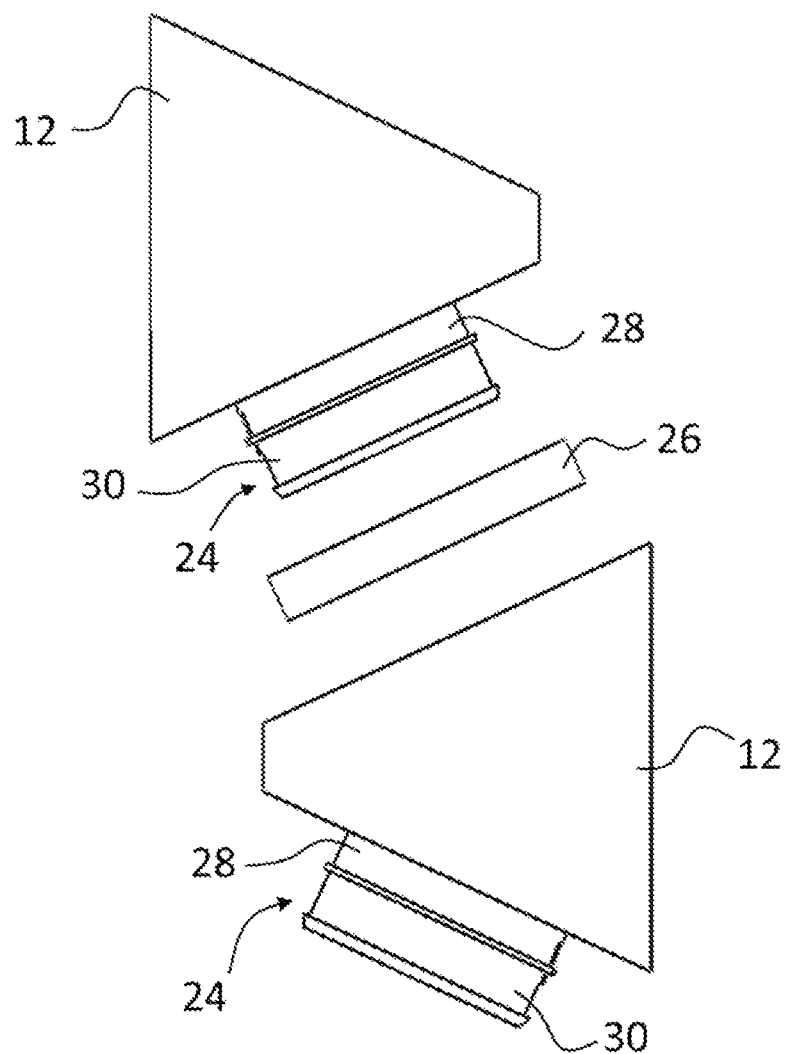
FIG. 4 illustrates an assembly view of two joints and a bearing.

The head 24 may include an opening 34 therein. The opening 34 may be positioned at the end of the head and may extend through the head 24 into the inner volume 32 of the joint 12. The head 24 may further include a through hole 36 and a divot 38. As shown in FIG. 2, the through hole 36 and divot 38 may be located at appropriate positions around the outer circumference of the head 24, such as positioned opposite one another on a circular head 24. The through hole 36 may comprise an indentation into the lower portion 30 and extending as an opening through the upper portion 28 into the inner volume 32 of the joint 12 The through hole 36 may extend through the inner volume forming a recess 37 in the inner wall of the joint 12. The recess 37 may extend all the way to the top 20, as shown in FIG. 3. The divot 38 may comprise an indentation in the lower portion 30 that terminates at or near the intersection of the upper portion 28 and lower portion 30.

When seated on the head 24, the bearing 26 may cover an outer portion of the through hole 36 and divot 38, leaving a bottom portion of each exposed at the proximal end of the lower portion 30.

In an embodiment, the arm 10 comprises a plurality of joints 12 having a variety of angular designs. As shown in FIGS. 6-10, the arm 10 may comprise a first joint 40, one or more intermediate joints 42, and a terminal joint 44. Each type of joint 40, 42, 44 may include a different geometry, described below.

Figure 6:
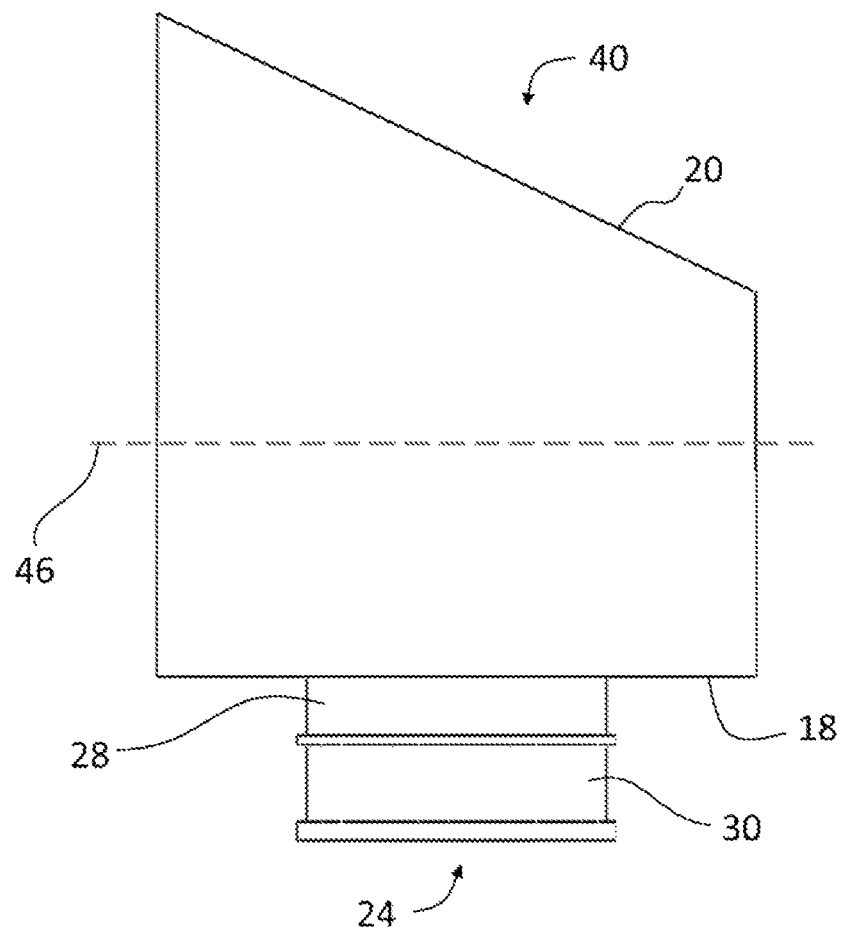
FIG. 6 illustrates a side view of a first joint.
Figure 7:
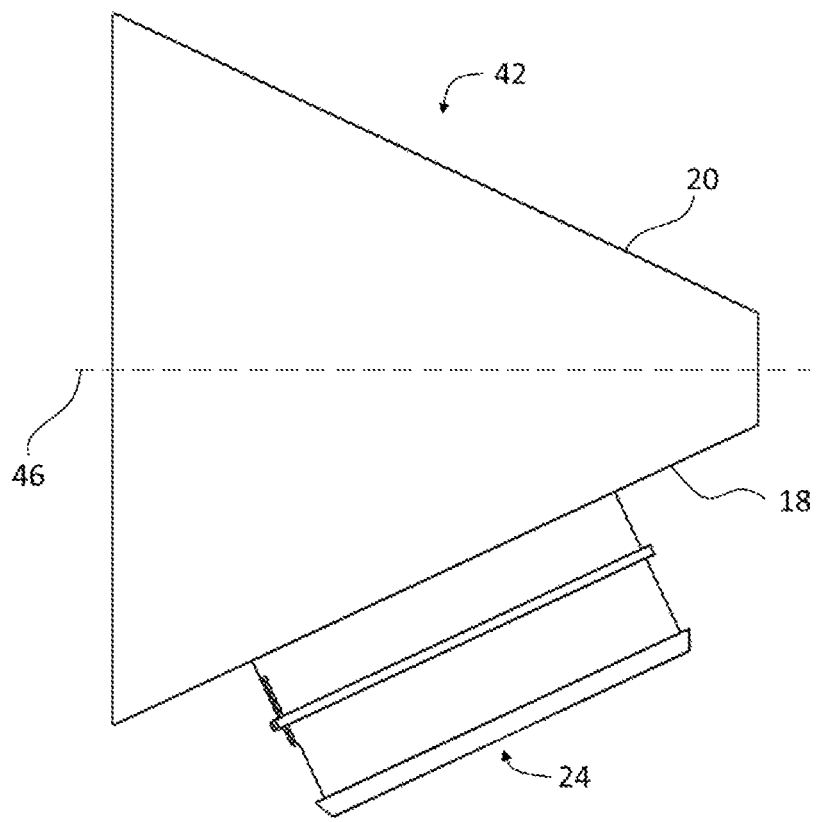
FIG. 7 illustrates a side view of an intermediate joint.
Figure 8:
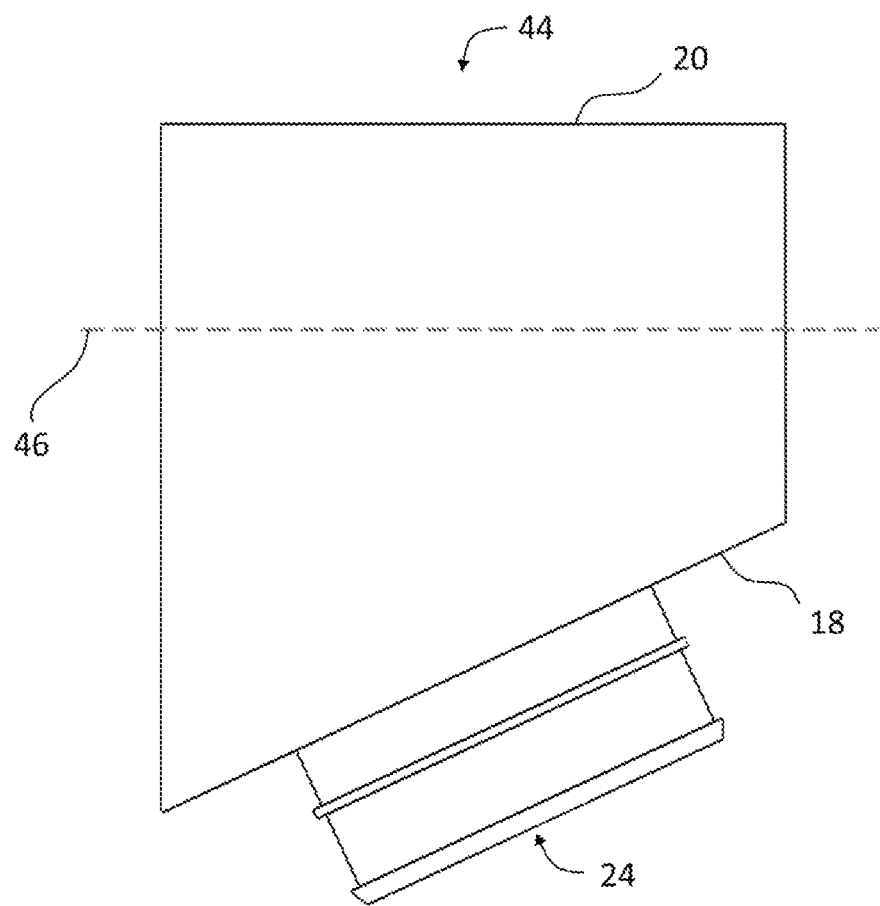
FIG. 8 illustrates a side view of a terminal joint.

The joints 12 may have a generally cylindrical shape. As shown in FIGS. 6-8, the first joint 40, intermediate joints 42, and terminal joint 44 may all include a theoretical normal plane 46. The normal plane 46 is defined as the plane that is oriented perpendicular to the outer walls 22 of each joint 12. For cylindrical joints 12 the normal plane 46 is defined as also perpendicular to the axis of the cylinder. The base 18 and top 20 may be arranged at a given angle with respect to the normal plane 46. For example, the base 18 or top 20 may be parallel to the normal plane 46 or arranged at a specified angle with respect thereto, as shown in the drawings and described below.

A first joint 40 is illustrated in FIG. 6. The first joint 40 includes a base 18 that is generally parallel to its normal plane 46. The top of the first joint 40 is angled with respect to the normal plane 46. For example, the top 20 of the first joint 40 may be arranged at an angle of 22.5 degrees with respect to the normal plane 46. However, it will be appreciated that the top 20 of the first joint 40 may be arranged at any appropriate angle with respect to the normal plane 46, such as between 10 degrees and 80 degrees.

An intermediate joint 42 is illustrated in FIG. 7. Both the base 18 and top 20 of the intermediate joint 42 are arranged at an angle with respect to the normal plane 46. In an embodiment shown in FIG. 7, the top 20 and base 18 may be arranged at opposite angles with respect to the normal plane 46. For example, the base may be arranged at an angle of 22.5 with respect to the normal plane 46 in a first direction and the top 20 may be arranged at an angle of 22.5 degrees with respect to the normal plane 46 in a second direction. However, it will be appreciated that both the base 18 and top 20 of the intermediate joint 42 may be arranged at any appropriate angle with respect to the normal plane 46.

A terminal joint 44 is illustrated in FIG. 8. The terminal joint 44 includes a top 20 that is generally parallel to its normal plane 46. The base 18 is angled with respect to the normal plane 46. For example, the base 18 of the terminal joint 44 may be arranged at an angle of 22.5 degrees with respect to the normal plane 46. However, it will be appreciated that the base 18 of the terminal joint 44 may be arranged at any appropriate angle with respect to the normal plane 46.

Figure 9:
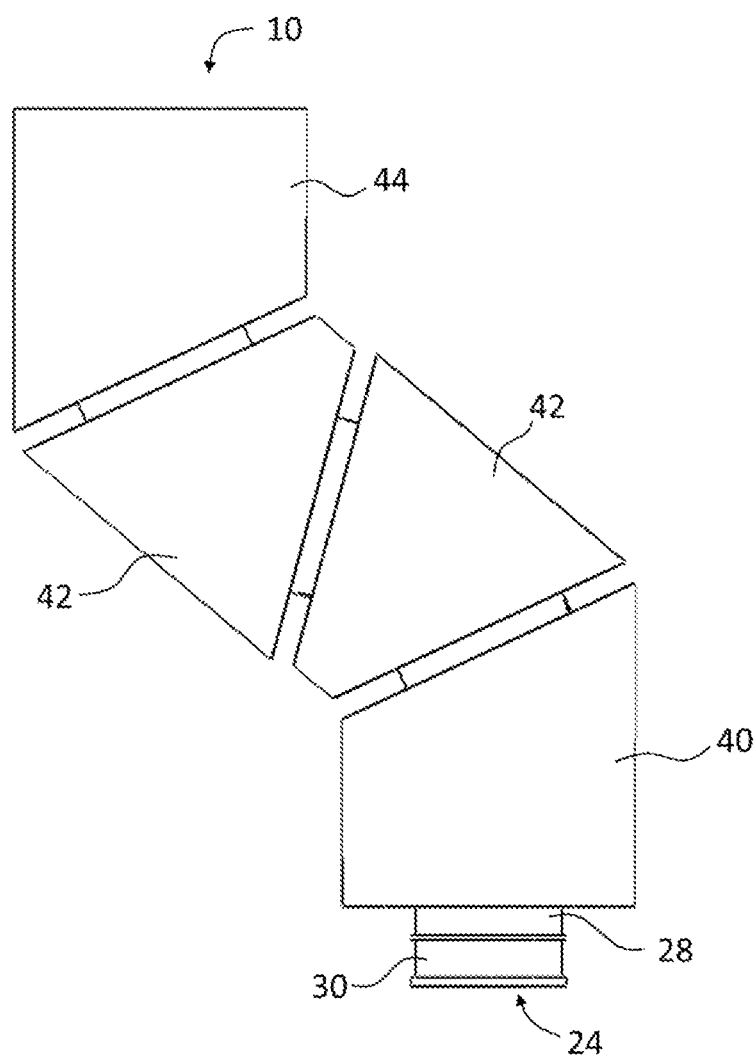
FIG. 9 illustrates the robot arm assembly in a multi-curved formation.
Figure 10:
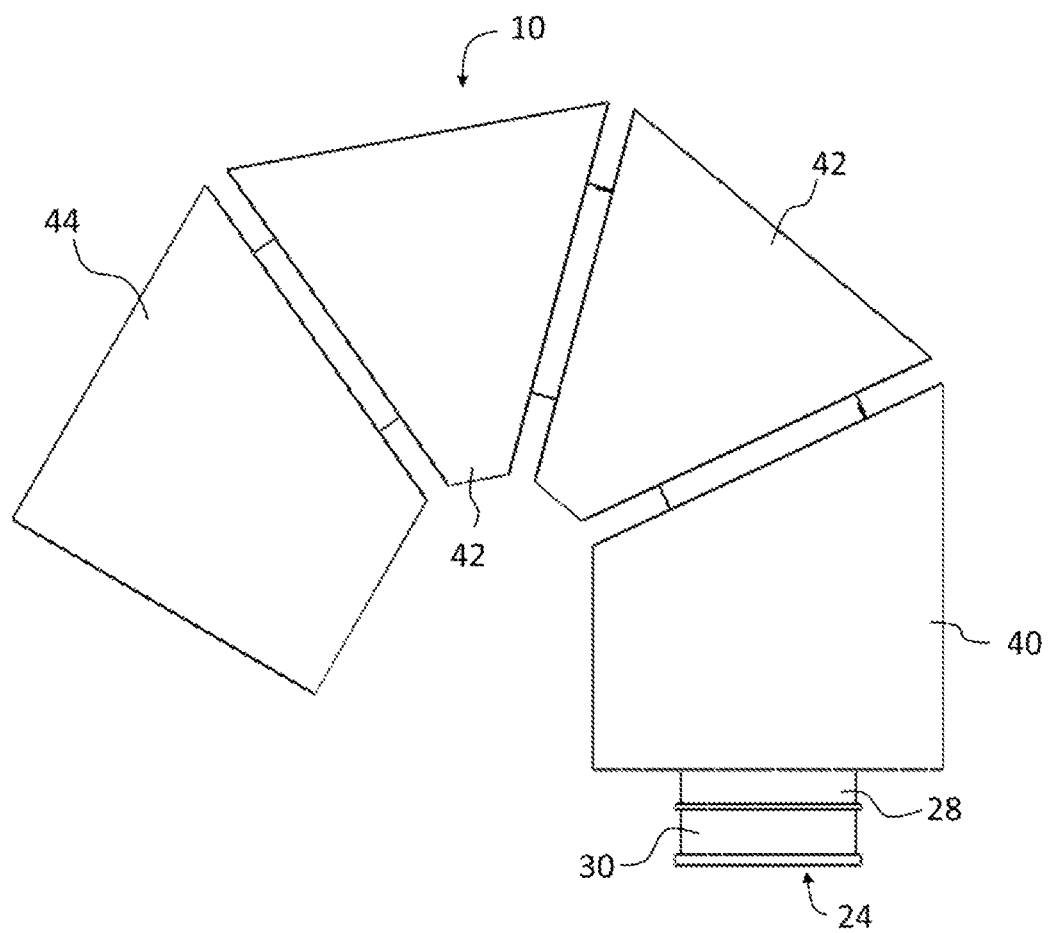
FIG. 10 illustrates the robot arm assembly in retroflexion.

The first joint 40, one or more intermediate joints 42, and a terminal joint 44 may be connected together to form an arm 10. The geometry of the arm 10 and spatial relation between the first and terminal joints 40, 44 may be manipulated by rotating adjacent joints, as shown in FIGS. 1, 9, and 10.

The joints 12 of the arm 10 may be controlled mechanically by a series of control wires 50. For example, a control wire or wires 50 may be connected to each joint 12 to control rotation of the joint 12 and thus the geometry of the arm 10. The control wires 50 may be formed of any appropriate flexible material, such as monofilament, braid, or steel wire.

Figure 11:
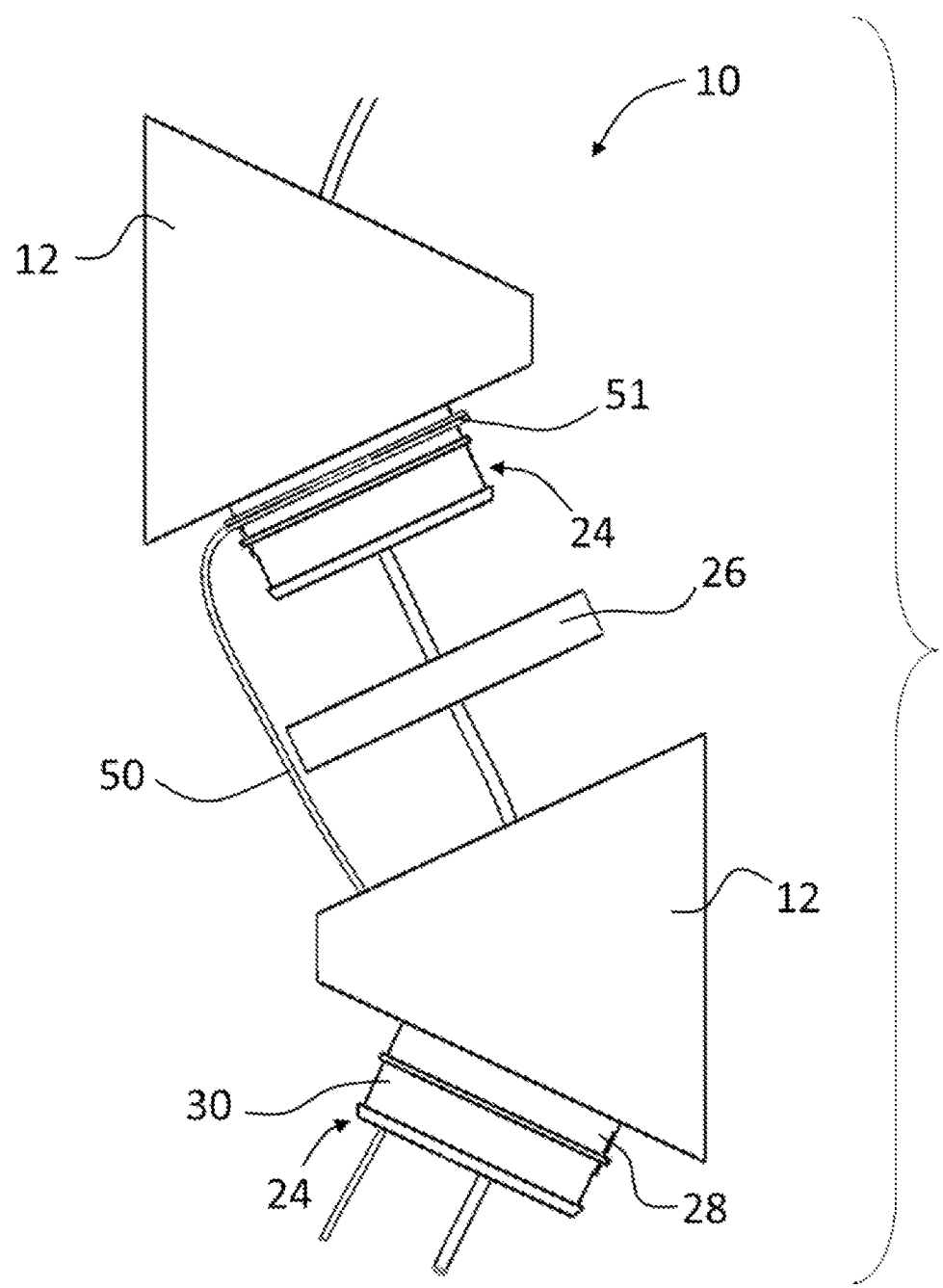
FIG. 11 illustrates a joint having attached internal control wires.

The control wire 50 for each joint may comprise a knot or fixed nodule. For example, a knot may be tied in a single control wire 50 or formed by tying two control wires 50 together. The knot may be located near the middle of the control wire 50 leaving approximately equivalent ends of the control wire 50 extending from each side of the knot. To attach the control wire to the joint 12, the knot may be placed in the divot 38 prior to connecting the bearing 26. The bearing 26 may then be placed onto the lower portion 30 thereby securing the knot in the divot 38 and attaching the control wire 50 to the joint 12. The two ends of the control wire 50 may then be wrapped around the portion of the head 24 between the bearing 26 and the base 18 to connect the control wire 50 to the joint 12. The control wire ends 50 may be wound in opposite directions, such as wound 1-4 times around the head to form a winding 51 as shown in FIG. 11, leaving long ends of the control wire 50. The control wire ends may then be inserted through the recess 37 of the adjacent joint 12 and down the adjacent joint's through hole 36 into its inner volume 32. From the adjacent joint's inner volume 32, the control wires 50 may then be routed through the opening 34 in the head 24 of the next adjacent joint 12 and through the openings 34 and inner volumes 32 of any remaining joints until routed entirely through the arm 10.

Figure 12:
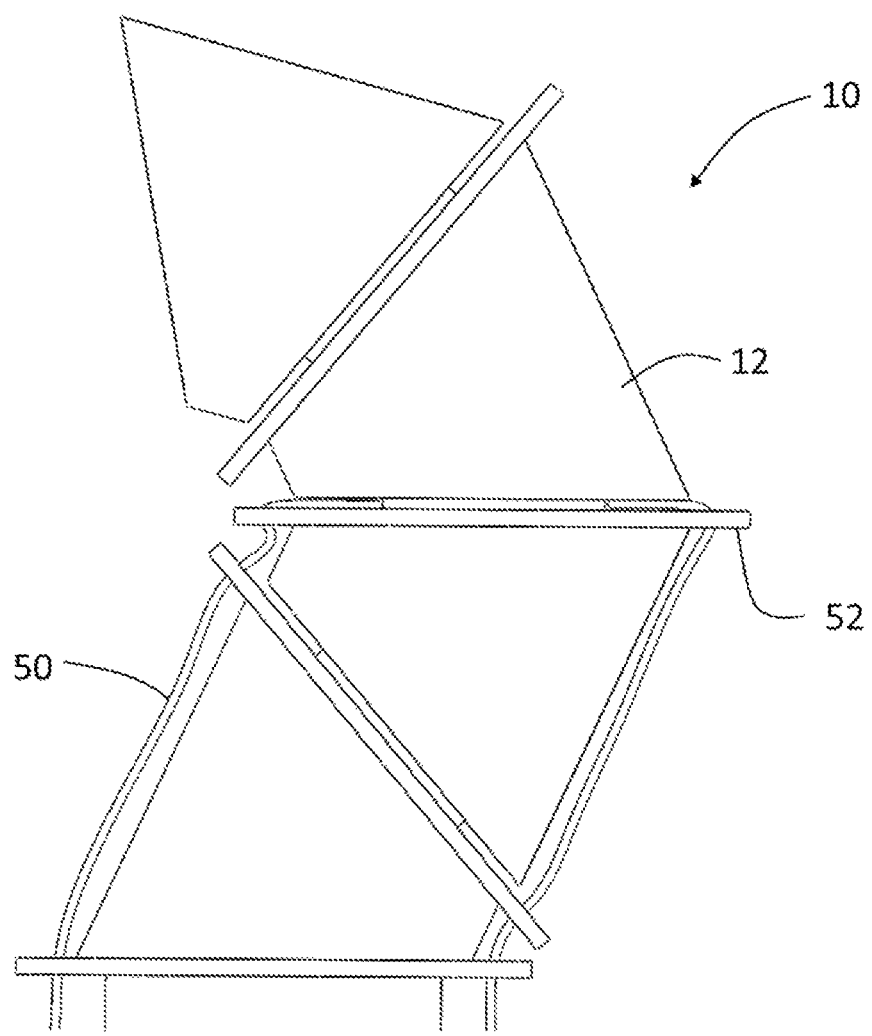
FIG. 12 illustrates the robot arm assembly with attached external control wires.
Figure 13:
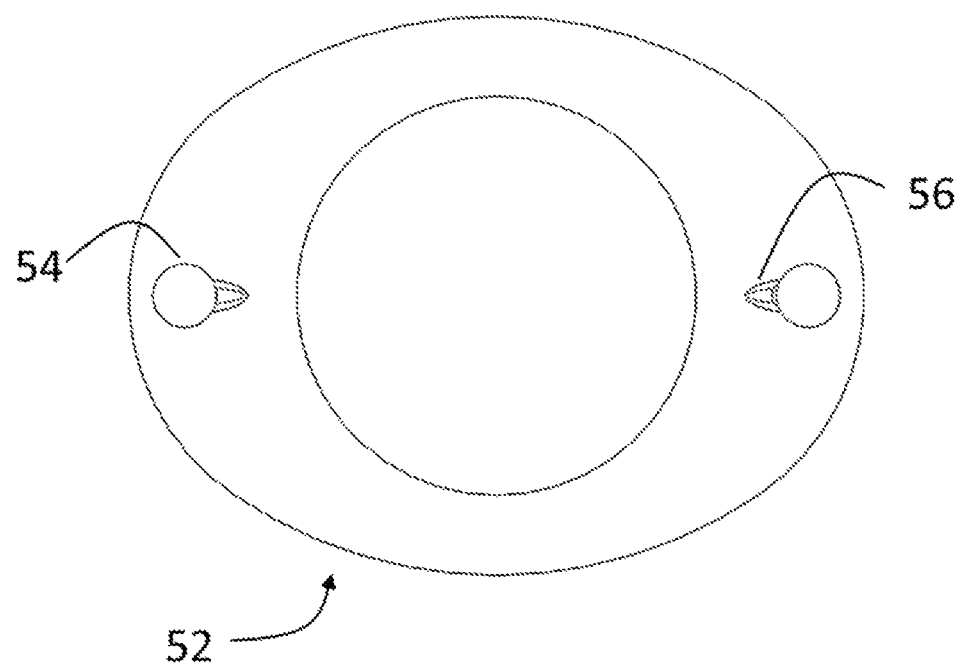
FIG. 13 illustrates the rotatable disc for external attachment of the control wires.
Figure 14:
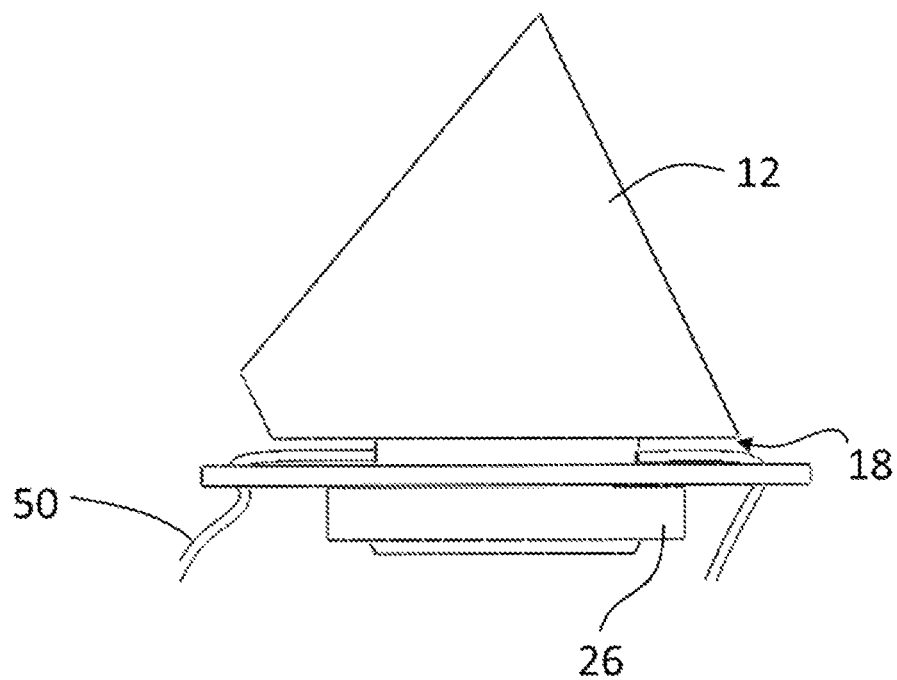
FIG. 14 illustrates an intermediate joint with externally attached control wires.

In an embodiment, the control wires 50 may be routed external to the arm 10 instead of internal, as described above. For example, a disc 52 may be positioned between two adjacent joints, as shown in FIGS. 12-14. A disc 52 may be located between each, some, or none of the adjacent joint in the set.

The disc 52 may have any appropriate shape, such as circular or ovular, with one or more portions of the disc protruding from the general footprint of the joint 12 that it is connected to. The discs 52 may have an opening or hole therein such that it includes an inner diameter defined as the diameter of the hole and an outer diameter defined as the diameter of the disc 52. The inner diameter of the disc 52 may be larger than the outer diameter of the head 24, and the outer diameter of the disc 52 may be larger than the diameter of the top 20 of the joint 12 such that at least a portion of the disc 52 extends beyond the footprint of the joint 12. The disc 52 may be positioned with the head 24 of the joint 12 extending through the opening to allow the disc 52 to rotate with respect to the head 24.

One or more through-holes 52 may be located on the disc 52 external to the joint 12 to allow connection and passage of the control wires 50. The through-holes 54 may include channels 56 that guide the control wires 50 to the appropriate space between the joint. These control wires 50 may be wrapped or wound around the portion of the head 24 between the bearing 26 and the base 18 in opposite directions 1-4 times, then routed through the space between adjacent joints to be external to the arm 10. To prevent the control wires 50 from crossing when the joints are turning, the disc 52 can rotate within the space between adjacent joints. Springs between the discs can be used to facilitate the rotation.

In an embodiment, the control wires 50 may connect to the joint 12 in a gear/belt fashion. For example, the wires 50 may comprise a belt having teeth to engage a gear. The head 24 may further include teeth configured to mate with the teeth of the belt. The belt and head may be mated such that movement of the belt rotates the joint 12 as desired.

In use, the arm 10 may be controlled through mechanical movement of the control wires 50 to control the rotation of each joint 12. For example, each joint may include two control wires 50, as described above. The first control wire may be pulled to rotate the joint 12 in a first direction and the second control wire 50 may be pulled to rotate the joint 12 in the opposite direction. The angled faces of the various joints 12 may allow the arm 10 to then take the desired shape.

It will be appreciated that the arm may be attached to a controlling mechanism. For example, the control wires 50 may be connected to controlling devices, such as motors or actuators, to measurably move the control wires 50 of each joint 12 to achieve the desired formation of the arm 10. It will be appreciated that the controlling mechanism maintains the tautness of each of the control wires 50. For example, tautness of control wires 50 for each joint 12 can be maintained by mechanical or electrical devices, such as springs or motors.

It will be appreciated that the arm may be easily attachable and detachable from a controlling mechanism. For example, the arm may be snap fit into the controlling mechanism to allow for disposability, cleaning, or interchangeability of the arm.

An end tool (not shown) may be connected to the terminal joint 44. The end tool may comprise any useful tool that may utilize the spatial navigation of the arm 10. The end tool may comprise a medical device, camera, or any other mechanical or electrical tool or other form of tool. Control wires, such as mechanical or electrical control wires, from the end tool may be routed through the arm in the same manner the arm control wires 50 are routed.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

Having thus described the invention, I claim:

1. A mechanical arm assembly comprising:
a plurality of joints interconnected to form the mechanical arm assembly, the plurality of joints comprising a first joint, one or more intermediate joints, and a terminal joint connected in consecutive series and each configured to rotate with respect to any respective adjacent joints;
wherein each joint includes a base, a top, and a sidewall interconnecting the base and the top;
wherein a normal plane of each joint is defined as generally perpendicular to the sidewall and wherein the base and top each are arranged at an angle with respect to the normal plane;
wherein the first joint is configured with its base generally parallel to its normal plane and its top at an angle between 10 and 80 degrees with respect to its normal plane;
wherein the intermediate joints are configured with their bases at an angle between 10 and 80 degrees in a first direction with respect to their normal plane and their tops at an angle between 10 and 80 degrees in a second direction, opposite the first direction, with respect to its normal plane;
wherein the terminal joint is configured with its base at an angle between 10 and 80 degrees with respect to its normal plane and its top generally parallel to its normal plane; and
a head protruding perpendicularly from the base of each joint; and
one or more control wires each connected to the head of a single joint, wherein the control wires are wound around the head, wherein mechanical movement of the control wires is configured to impart rotational movement on its corresponding joint to rotate the joint with respect to an adjacent joint and around an axis that is normal to the top of an adjacent joint.

2. The mechanical arm assembly of claim 1 further comprising an end tool connected to the terminal joint.

3. The mechanical arm assembly of claim 2, wherein the end tool comprises one of a medical device or a camera.

4. The mechanical arm assembly of claim 1 further comprising a head protruding from the base and an opening in the top of each intermediate joint and the terminal joint, wherein the head of each intermediate and terminal joint is each configured to be inserted into the opening in the tops of the respective adjacent intermediate or base joints.

5. The mechanical arm assembly of claim 4 further comprising a bearing positioned around the head of each intermediate and terminal joint, wherein the bearing is configured to insert into the opening in the top of each respective adjacent intermediate and first joint to form a rotational connection between adjacent joints.

6. The mechanical arm assembly of claim 4 wherein each joint includes an opening in the top extending through the base, and wherein the one or more control wires are each connected to a single controlled joint in the mechanical arm assembly, and further wherein each control wire extends through the openings of each intermediate joint between the controlled joint and the first joint and through the opening in the first joint.

7. The mechanical arm assembly of claim 4 further comprising a disc having a hole therein positioned around the head such that the head protrudes through the hole, wherein the disc is rotatable with respect to the head.

8. The mechanical arm assembly of claim 7, wherein the disc comprises one or more through-holes and wherein the one or more control wires are routed through respective through-holes.

9. The mechanical arm assembly of claim 8, wherein the disc is positioned between the bearing and the base of the joint.

10. The mechanical arm assembly of claim 1 wherein the opening in the base through the top forms an outer ring in the top, wherein the outer ring includes a recess in its inner perimeter, and further wherein the control wire from an adjacent joint passes through the recess into the opening.

11. The mechanical arm assembly of claim 1, wherein each one or more control wire includes a knot therein and wherein the each head includes a divot therein, and further wherein the knot of each one or more control wire is positioned in the divot of each corresponding head and each respective bearing is positioned around the respective heads to hold the respective control wires in place.

12. The mechanical arm assembly of claim 1 wherein the opening in the base through the top forms an outer ring in the top, wherein the outer ring includes a recess in its inner perimeter, and further wherein the control wire from an adjacent joint passes through the recess into the opening.

13. The mechanical arm assembly of claim 1 wherein the one or more control wires comprises two control wires connected to each joint in the mechanical arm assembly.

14. A mechanical arm assembly comprising:
a plurality of joints interconnected to form the mechanical arm assembly, the plurality of joints comprising a first joint, one or more intermediate joints, and a terminal joint connected in consecutive series and each configured to rotate with respect to any respective adjacent joints;
wherein each joint includes a base, a top, a sidewall interconnecting the base and the top, and an opening in the top extending through the base;
a head protruding perpendicularly from the base of each joint;
one or more control wires each connected to the head of a single controlled joint in the mechanical arm assembly, wherein the control wires are wound around the head, wherein each control wire extends through the openings of each intermediate joint between the controlled joint and the first joint and through the opening in the first joint; and
wherein the control wires are configured to control rotational movement of the controlled joint around an axis that is normal to the top of an adjacent joint.

15. The mechanical arm assembly of claim 14 wherein the one or more control wires comprises one control wire connected to each joint in the mechanical arm assembly.

16. The mechanical arm assembly of claim 14, wherein the head of each intermediate and terminal joint is configured to be inserted into the opening of the respective adjacent intermediate or base joint.

17. The mechanical arm assembly of claim 16 further comprising a bearing positioned around the head of each intermediate and terminal joint, wherein the bearing is configured to insert into the opening in the top of each respective adjacent intermediate or base joint to form a rotational connection between adjacent joints.

18. The mechanical arm assembly of claim 14, wherein each one or more control wire includes a knot therein and wherein each head includes a divot therein, and further wherein the knot of each one or more control wire is positioned in the divot of each corresponding head and each respective bearing is positioned around the respective heads to hold the respective control wires in place.

19. The mechanical arm assembly of claim 14, wherein the first joint is configured with its base generally parallel to its normal plane and its top at an angle between 10 and 80 degrees with respect its normal plane;
   wherein the intermediate joints are configured with their bases at an angle between 10 and 80 degrees in a first direction with respect their normal plane and their tops at an angle between 10 and 80 degrees in a second direction, opposite the first direction, with respect its normal plane; and
   wherein the terminal joint is configured with its base at an angle between 10 and 80 degrees with respect its normal plane and its top generally parallel to its normal plane and its top.

20. A mechanical arm assembly comprising:
   a plurality of joints interconnected to form the mechanical arm assembly, the plurality of joints comprising a first joint, one or more intermediate joints, and a terminal joint connected in consecutive series and each configured to rotate with respect to any respective adjacent joints;
   wherein each joint includes a base, a top, a sidewall interconnecting the base and the top, and an opening in the top;
   a head protruding perpendicularly from the base of each joint, wherein the head of each intermediate and terminal joint is configured to be inserted into the opening of the respective adjacent intermediate or base joint;
   a disc having a hole therein positioned around the head such that the head protrudes through the hole, wherein the disc is rotatable with respect to the head;
   one or more control wires each connected to a disc on a controlled joint in the mechanical arm assembly and connected to the head, wherein the control wires are wound around the head, each control wire extending toward the first joint and positioned exterior to each joint in the mechanical arm assembly; and
   wherein the control wires are configured to control rotational movement of the controlled joint around an axis that is normal to the top of an adjacent joint.

21. The mechanical arm assembly of claim 20, wherein the disc comprises one or more through-holes and wherein the one or more control wires are routed through respective through-holes.

22. The mechanical arm assembly of claim 21, further comprising a channel adjacent to the through holes, wherein the channel is configured to guide the control wires toward the head.

23. The mechanical arm assembly of claim 22 wherein the control wires are wound around the head 1-4 times.

24. The mechanical arm assembly of claim 20 further comprising a bearing positioned around the head of each intermediate and terminal joint, wherein the bearing is configured to insert into the opening in the top of each respective adjacent intermediate or base joint to form a rotational connection between adjacent joints.

25. The mechanical arm of claim 24, wherein the disc is positioned between the bearing and the base of the joint.

26. The mechanical arm assembly of claim 20, wherein the first joint is configured with its base generally parallel to its normal plane and its top at an angle between 10 and 80 degrees with respect its normal plane;
   wherein the intermediate joints are configured with their bases at an angle between 10 and 80 degrees in a first direction with respect their normal plane and their tops at an angle between 10 and 80 degrees in a second direction, opposite the first direction, with respect its normal plane; and
   wherein the terminal joint is configured with its base at an angle between 10 and 80 degrees with respect its normal plane and its top generally parallel to its normal plane and its top.

* * * * *

UNITED STATES PATENT AND TRADEMARK OFFICE
CERTIFICATE OF CORRECTION

PATENT NO.       : 11,104,011 B2
APPLICATION NO.  : 15/811008
DATED            : August 31, 2021
INVENTOR(S)      : Robert Chisena Page 1 of 1

It is certified that error appears in the above-identified patent and that said Letters Patent is hereby corrected as shown below:

In the Claims

Column 10, Line 44 delete "plane and its top." and insert --plane.--

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*